United States Patent [19]

Grazioso et al.

[11] Patent Number: 4,661,525

[45] Date of Patent: Apr. 28, 1987

[54] PROCESS FOR PRODUCING LOWER ALIPHATIC ALCOHOLS

[75] Inventors: Michael V. Grazioso, Poughkeepsie; Edwin R. Kerr, deceased, late of Wappinger, both of N.Y., by Myra L. Kerr, executor

[73] Assignee: Texaco Inc., White Plains, N.Y.

[21] Appl. No.: 728,636

[22] Filed: Apr. 29, 1985

Related U.S. Application Data

[63] Continuation-in-part of Ser. No. 594,053, Mar. 28, 1984, abandoned.

[51] Int. Cl.$^4$ .............................................. C07C 27/06
[52] U.S. Cl. .................................... 518/714; 502/206; 502/211; 502/255; 502/305
[58] Field of Search ........................................ 518/714

[56] References Cited

U.S. PATENT DOCUMENTS

| | | | |
|---|---|---|---|
| 2,183,146 | 12/1939 | Michael | 518/714 |
| 4,298,354 | 11/1981 | Hardman et al. | 44/56 |
| 4,459,369 | 7/1984 | Passariello | 518/713 |

FOREIGN PATENT DOCUMENTS 1155463 10/1983 Canada .
119609 9/1984 European Pat. Off. .

OTHER PUBLICATIONS

Tatsumi et al, Chemistry Letters, pp. 685-688, May 1984.

*Primary Examiner*—Howard T. Mars
*Attorney, Agent, or Firm*—Robert A. Kulason; James J. O'Loughlin

[57] ABSTRACT

A method is provided for preparing a mixture of lower aliphatic alcohols characterized by containing a substantial proportion of aliphatic alcohols having from 2 to 6 carbon atoms by reacting a mixture of carbon monoxide and hydrogen under suitable conditions of temperature and pressure in the presence of a catalyst comprising molybdenum and a metal from the group consisting of cobalt, iron and nickel, said catalyst being modified by the addition of a promoter from the class consisting of potassium, cesium and rubidium, said promoter being employed at a concentration ranging from about 1.8 to 13.0 micromoles of said alkali per square meter of surface area of said catalyst.

18 Claims, No Drawings

PROCESS FOR PRODUCING LOWER ALIPHATIC ALCOHOLS

This application is a continuation-in-part of application Ser. No. 594,053, filed on Mar. 28, 1984, now abandoned.

BACKGROUND OF THE INVENTION

1. Field of the Invention

This invention relates to a process for preparing lower aliphatic alcohols. More particularly, this invention relates to the production of a mixture of lower aliphatic alcohols characterized by containing a substantial proportion of alcohols having from 2 to 6 carbon atoms.

Lower aliphatic alcohols have been proposed as fuel extenders or as replacements for gasoline for fueling internal combustion engines. Certain mixtures of lower aliphatic alcohols have the EPA approval for use and are currently being marketed in the United States. The lower aliphatic alcohols can be produced from domestically available non-petroleum sources, and their use in fuels would serve to lessen the dependence on the nation on imported petroleum and petroleum products.

Hydrogen and carbon monoxide, or a synthesis gas mixture of hydrogen and carbon monoxide, can be reacted to form lower aliphatic alcohols. The synthesis gas feed stream can be produced from non-petroleum sources, such as coal, biomass or other hydrocarbonaceous materials. The synthesis gas mixture itself is produced in a partial oxidation reaction of the hydrocarbonaceous material in commercially available processes such as coal gasification.

Numerous catalytic processes have been studied in attempts to provide a viable process for the production of aliphatic alcohols from synthesis gas or from a mixture of hydrogen and carbon monoxide. Heretofore, the emphasis has been primarily directed to the production of methanol. In contrast, the present process is directed to a method for producing an alcohol mixture containing a substantial amount of aliphatic alcohols having from 2 to 6 carbon atoms. Under selected reaction conditions, this process is effective for producing a fraction of higher aliphatic alcohols, i.e. an alcohol fraction consisting of $C_2$ to $C_6$ alcohols, which represents the major or predominant alcohol production in this process.

2. Disclosure Statement

U.S. Pat. No. 1,201,850 discloses a method for the production of hydrocarbons and oxygenated compounds of hydrocarbons by passing an oxide of carbon and hydrogen over a heated catalytic agent under a pressure exceeding 5 atmospheres. A number of catalytic materials are disclosed as well as the fact that a basic compound, such as an alkaline metal hydroxide, can be used with the prescribed catalytic agents.

U.S. Pat. No. 1,625,929 discloses a process for producing methanol in which the catalyst contains copper, cobalt and a metallic halide.

U.S. Pat. No. 3,345,427 discloses a dehydrogenation catalyst and process in which the catalyst consists of nickel, molybdenum and alkali metal oxides on an alumina support.

U.S. Pat. No. 4,096,164 discloses a process for reacting hydrogen and carbon monoxide in the presence of a solid catalyst comprising rhodium with molybdenum or tungsten to produce two carbon atom oxygenated hydrocarbons in which ethanol is the major component.

U.S. Pat. No. 4,199,522 discloses a Fischer-Tropsch process for producing olefins and this disclosure is incorporated herein by reference.

U.S. Pat. Nos. 4,235,801 and 4,246,186 disclose the production of alcohols from a mixture of carbon monoxide and hydrogen in the presence of a rhenium catalyst.

U.S. Pat. No. 4,380,589 discloses a Fischer-Tropsch process for producing hydrocarbons with improved selectivity to $C_2$-$C_4$ olefins by contacting hydrogen and carbon monoxide in the presence of a catalyst. The catalyst disclosed comprises molybdenum, a promoter comprising alkali or alkaline earth metal, and a binder comprising an iron-containing calcium aluminate cement.

EPA 119609 discloses a process for producing alcohols from synthesis gas using a catalyst containing molybdenum with tungsten, rhenium and an alkali metal. This disclosure is incorporated herein by reference. E.P. 79132 discloses a similar process in which the catalyst contains rhenium, molybdenum and potassium.

Previous catalytic processes have been notably effective for converting carbon monoxide and hydrogen feedstocks into hydrocarbons or methanol, but none have been particularly effective for providing high yields of a lower aliphatic alcohol mixture characterized by having a substantial amount of alcohols having from 2 to 6 carbon atoms along with the co-produced methanol.

SUMMARY OF THE INVENTION

It has now been discovered that a mixture of carbon monoxide and hydrogen can be reacted to form a mixture of lower aliphatic alcohols containing a substantial amount of aliphatic alcohols having from 2 to 6 carbon atoms. This reaction is conducted by contacting a feed mixture such as synthesis gas with a novel catalyst composition which exhibits good selectivity for the production of $C_2$-$C_6$ aliphatic alcohols under suitable conditions of temperature and pressure. The effective catalyst composition comprises a mixture of molybdenum and a heavy metal from the group consisting of cobalt, iron and nickel. This heavy metal catalyst composition is modified by the addition of a critical amount of an alkali metal promoter from the class consisting of potassium, cesium and rubidium in an amount ranging from about 1.8 to 13.0 micromoles of alkali per square meter of surface area of the catalyst thereby forming a promoted or modified catalyst.

DETAILED EMBODIMENTS OF THE INVENTION

In accordance with this invention, a mixture of carbon monoxide and hydrogen as, for example, a synthesis gas mixture of said reactants, is reacted over a catalyst comprising molybdenum and a metal from the group consisting of cobalt, iron and nickel which has been modified by the addition of a promoter from the group consisting of potassium, cesium and rubidium, said promoter being employed at a concentration ranging from about 1.8 to 13.0 micromoles of alkali per square meter of surface area of the catalyst. The nature and the concentration of the promoter on the catalyst are critical. Concentrations of promoter outside of the prescribed range results in a sharp reduction in the effectiveness of this process.

The critical concentration range for the alkali promoter is an amount from about 1.8 to 13.0 micromoles of alkali per square meter of surface area of the catalyst. A preferred alkali promoter concentration is from 2.2 to 10.0 micromoles of alkali per square meter of catalyst surface area. A particularly preferred alkali promoter concentration is from about 2.5 to about 9.0 micromoles of alkali per square meter of catalyst surface area.

The catalyst can be prepared in a number of ways known in the art. In general, the use of a catalyst support or carrier comprising a relatively refractory, porous, adsorptive and high surface area material is preferred. Conventional carriers or supports, such as alumina, silica, titania, magnesia, silica-alumina and boron phosphates, are suitable support materials for preparing the catalyst for this process. The disclosure in U.S. Pat. No. 4,098,683 is illustrative and is incorporated herein by reference.

A preferred method for preparing the catalyst is to impregnate a carrier, such as alumina, with a source of molybdenum generally in the form of a soluble salt and then with a metal from the class of cobalt, nickel and iron, generally also in the form of a soluble salt. The impregnation of the carrier with the catalyst metals can be done simultaneously or step-wise. The impregnated carrier is dried and then calcined according to known procedures.

The catalyst thus prepared is then modified, i.e. treated or impregnated, with an alkali metal promoter from the group of potassium, cesium or rubidium generally in the form of a salt. The treated or modified catalyst is then subjected to reduction with hydrogen gas generally by heating the promoted catalyst at a temperature between about 300° and 500° C. for an extended period, usually 2 to 8 hours.

The catalyst comprises from about 5 to 50 weight percent of molybdenum calculated as molybdenum trioxide and from about 0.3 to 15 weight percent of a metal from the group consisting of cobalt, nickel and iron calculated as the respective oxide CoO, NiO or $Fe_2O_3$ or mixtures thereof with the balance being the support. A preferred catalyst composition comprises from about 7 to 30 weight percent of molybdenum trioxide and from about 0.5 to 10 weight percent of cobalt, nickel, or iron oxide or a combination of the latter. Still more preferred is a catalyst comprising from about 7 to 12 weight percent molybdenum and from about 1.5 to 5 weight percent of a metal from the group consisting of cobalt, iron and nickel or mixtures thereof calculated as hereinabove described.

The catalyst should have a surface area of 125 $m^2$/gm (square meters per gram of catalyst) or more. A more effective catalyst will have a surface area from about 150 to 350 $m^2$/gm and the most preferred will have a surface area from about 160 to 300 $m^2$/gm.

Alternatively, a commercially available catalyst comprising molybdenum and one or more of the metals from the class consisting of cobalt, nickel and iron meeting the foregoing specifications can be impregnated or modified by treatment with the prescribed alkali metal and then reduced under hydrogen gas and other conditions noted above.

The carbon monoxide and hydrogen employed to form the lower aliphatic alcohols in this process can be provided from any available source. One particularly useful source is synthesis gas produced in the gasification of hydrocarbonaceous materials, such as coals and biomass. An effective gasification process is described in U.S. Pat. No. 3,544,291 wherein a hydrocarbonaceous fuel is partially oxidized with a free oxygen-containing gas in a gas generator. In general, the mole ratio of hydrogen to carbon monoxide employed in this process should range from about 0.1 to 50 moles of hydrogen per mole of carbon monoxide with the preferred ratio being from about 0.5 to 20 moles of hydrogen per mole of carbon monoxide.

The reaction conditions for effecting the conversion of the carbon monoxide-hydrogen feed into lower aliphatic alcohols employing the prescribed catalyst of the invention include a reaction temperature ranging from about 240° to about 400° C. with a more preferred temperature range being from about 300° to about 360° C., and the most preferred range being from about 310° to 350° C. The effective pressures range for this process are from about $3.4 \times 10^6$ Pa (500 psi) to about $2.4 \times 10^7$ Pa (3500 psi). The preferred pressure range is from about $5.1 \times 10^6$ Pa (750 psi) to about $1.7 \times 10^7$ Pa (2500 psi).

The space velocity employed to effect the conversion of carbon monoxide and hydrogen over the prescribed catalyst to the aliphatic alcohols is a vital feature of this process. In general, the space velocity, that is the volume of gas passed through a given volume of catalyst per hour expressed as GHSV($hr^{-1}$), must be at least 1000. A preferred range is from about 5000 to about 50,000. A highly effective process is realized when the space velocity employed ranges from about 10,000 to about 30,000. Under preferred conditions the ratio of weight percent of $C_2$–$C_6$ alcohols to weight percent methanol can exceed 1, and more preferrably can be from 1.25 to 2.

The present invention is more fully described in the following Examples. In the Examples, the reaction was carried out in a 0.5 liter stainless steel Berty type recirculating gradientless reactor from Autoclave Engineers. (Erie, Pa.) The product emerging from the stainless steel reactor was then sent through a condensor which liquefied the alcohol and water products. The resulting liquid was analyzed by gas chromatography. The noncondensable gas was generally analyzed by gas chromatography. Set forth in the Table is the composition of the catalyst, the reaction conditions and the selectivity to carbon dioxide, to $C_1$–$C_6$ hydrocarbons, to methanol and to $C_2$–$C_6$ alcohols. In addition, the weight ratio of $C_2$–$C_6$ alcohol production to methanol production is given as well as the $C_2$ and higher alcohol production expressed as grams of alcohol/gram of catalyst per hour (G/G-hr).

EXAMPLE I

A catalyst was prepared by impregnating a commercially available catalyst comprising cobalt and molybdenum on an alumina carrier with a solution of potassium carbonate. The catalyst was made by Armak Catalyst Division, Pasadena, Tex. and sold under the name Ketjen KF 124 LD. This catalyst is characterized by having a surface area of about 280 square meters per gram. The potassium carbonate solution was made by dissolving 2.5 grams of potassium carbonate in 50 cc of distilled water and this solution was added to 97.5 grams of the catalyst. The impregnated catalyst was dried in a forced air oven at about 150° C. for about 3 hours. The chemical analysis of the catalyst is set forth in the Table under Example I.

About 20 cc of this catalyst was tested in a Berty recycle reactor. The catalyst was reduced for about 4 hours at a temperature of about 400° C. and at pressure of about 1500 psig with a hydrogen gas flow of about 5.0 liters per minute. The catalyst was then heated to a temperature of about 343° C. and subjected to a mixture of hydrogen and carbon monoxide in a ratio of about 2:1, at a pressure of about $1 \times 10^7$ Pa (1,500 psi) and at a GHSV rate of about 28,000. The selectivity to carbon dioxide, hydrocarbons, methanol and alcohols containing 2 to 6 carbon atoms is set forth in the Table. The alcohol production in grams of alcohol per grams of catalyst per hour, and the ratio of weight percent alcohols of two to six carbon atoms to the weight percent of methanol is also set forth in the Table.

EXAMPLE II

A second catalyst was made as in Example I however, the catalyst was impregnated with a solution made by dissolving 5.0 grams of potassium carbonate in 50 cc of distilled water which was added to about 95.0 grams of the catalyst. The impregnated catalyst was treated as in Example I and contacted with a mixture of hydrogen and carbon monoxide as set forth in Example I. The results of this reaction are set forth in the Table.

EXAMPLE III

A catalyst was made as in Example I however, it was impregnated with a solution comprising 10 grams of potassium carbonate dissolved in 50 cc of the distilled water which had been added to 90.0 grams of the catalyst. The catalyst was treated as in Example I and then contacted with a mixture of hydrogen and carbon monoxide under the same conditions as in Example I. The results of this run is set forth in the Table.

EXAMPLE IV

A catalyst was made as in Example I however, 30 grams of potassium carbonate were dissolved to 90 cc of distilled water and this was added to about 170 grams of the catalyst. The resulting catalyst was treated as in Example I and then subjected to a mixture of hydrogen and carbon monoxide as in Example I. The results of this run are set forth in the Table.

EXAMPLE V

A catalyst was made as in Example I however, 20 grams of potassium carbonate were dissolved in 45 cc of water and this was added to 80 grams of the catalyst. The resulting impregnated catalyst was treated as in Example I, and then subjected to a mixture of hydrogen and carbon monoxide as set forth in Example I. The results are set forth in the Table.

A review of the results of Examples I-V as set forth in the Table shows that at small $\mu$-mole quantities of potassium, the alcohol production, selectivities towards alcohols and ratio of $C_2$-$C_6$ alcohols to methanol is very low (Example I). As the $\mu$-moles of potassium present in the cobalt-molybdenum catalyst is increased the production of alcohols especially $C_2$-$C_6$ alcohols increases to a point (Examples II and III) and then as the $\mu$-moles of potassium further increases, the production of alcohols drops off (Examples IV-V). Examples I-V show that within a critical range, the addition of potassium to a cobalt molybdenum catalyst makes the catalyst more selective towards alcohols and increases the production of alcohols from a mixture of carbon monoxide and hydrogen.

EXAMPLE VI (Comparative)

10 cc of a catalyst comprising cobalt and molybdenum on an alumina base, similar to that of Example I, but without the addition of potassium, cesium, rubidium, strontium or other metals was diluted with 90 cc of alpha alumina and packed into a 2.5 cm ID tubular reactor, then subjected to the hydrogen and carbon monoxide mixture of Example I. No alcohols were produced.

EXAMPLE VII (Comparative)

When a sample of alpha alumina as used in Example VI to dilute the catalyst was treated as in Example VI but without the addition of any promoter such as potassium and was then subjected to the hydrogen and carbon monoxide mixture of Example I, no alcohols were produced.

Examples VI and VII show that the cobalt-molybdenum catalyst and the alpha alumina used as diluent are both ineffective for producing alcohols under the conditions of this process.

EXAMPLE VIII (Comparative)

About 85 grams of a catalyst comprising a molybdenum compound on an alumina base, sold under the name Harshaw Mo 1201 was impregnated with a aqueous solution of about 15 grams of potassium carbonate dissolved in 25 cc of water. The resulting catalyst was dried in an oven at about 110° C. The catalyst was diluted and treated as in Example VI and subjected to a hydrogen and carbon monoxide atmosphere as in Example I. The results are set forth in the Table.

EXAMPLE IX (Comparative)

A catalyst was made by impregnating the alumina base with a cobalt nitrate solution. The impregnated alumina was then dried and then calcined for about 2 hours at about 375° C. and for about 3 hours at about 475° C. The calcined material was then impregnated with about 15% by weight potassium carbonate as an aqueous solution and finally air dried at about 230° C. The catalyst was diluted as in Example VI and then contacted with a carbon monoxide hydrogen atmosphere as in Example I and the results are set forth in the Table.

As can be seen from Examples VIII and IX, a molybdenum catalyst promoted with potassium or a cobalt catalyst promoted with potassium are both inactive for the production of alcohols. This shows that the present invention, the cobalt-molybdenum catalyst promoted with potassium, is highly effective while the lack of molybdenum, cobalt or potassium makes the catalyst inactive for the production of alcohols.

EXAMPLE X

A catalyst was made as in Example I, however, instead of using potassium carbonate, cesium carbonate was used. The cesium carbonate solution was made by dissolving 5 grams of cesium carbonate into about 30 cc of water which added to about 45.0 grams of the cobalt-molybdenum catalyst of Example I. The catalyst was treated as in Example I and then subjected to the carbon monoxide and hydrogen atmosphere of Example I. The results are set forth in the Table.

EXAMPLE XI

An impregnated catalyst was made as in Example X however, the solution of cesium carbonate used was made by dissolving 10 grams of cesium carbonate into 20 cc of water which was then added to 46.5 grams of the catalyst. The impregnated catalyst was then treated as in Example I and then was subjected, as in Example I, to an atmosphere of hydrogen and carbon monoxide. The results are set forth in the Table.

EXAMPLE XII

A catalyst was prepared by adding to about 42.5 grams of Ketjen KF 124 LD to a solution of cesium carbonate which had been prepared by dissolving 14.0 grams of cesium carbonate into 20 cc of water. The impregnated catalyst was dried in a vacuum oven for several hours at about 135° C. The catalyst was then treated as in Example I, and then subjected to the hydrogen and carbon monoxide atmosphere of Example I. The results are set forth in the Table.

EXAMPLE XIII

A catalyst was made as in Example X however, the cesium carbonate solution was made by adding 18 grams of cesium carbonate to 20 cc of water which was in turn added to 38.5 grams of the cobalt-molybdenum catalyst of Example I. The catalyst was then treated as in Example I and subjected to the hydrogen and carbon monoxide atmosphere of Example I. The results are set forth in the Table.

Examples X—XIII show that the use of a critical quantity of cesium to promote the cobalt-molybdenum catalyst results in the production of the desired alcohols. As can be seen from the alcohol production figures in the Table, when too little or too much of the cesium is used the alcohol production decreases. It is apparent from the examples that the level of cesium in the catalyst is critical to the production of the desired alcohols and that as the quantity of cesium in the catalyst moves out of the critical range, the production of alcohols drops off.

EXAMPLE XIV

A catalyst was made as in Example I however, instead of using potassium carbonate, rubidium carbonate was used. The manufacture of the catalyst following the procedure of Example I, 25 grams of rubidium carbonate were dissolved in 40 cc of water and this added to 75 grams of the Ketjen KF 124 LD of Example I. The catalyst was treated as in Example I and loaded into the reactor as in Example VI and then subjected to the carbon monoxide and hydrogen atmosphere of Example I. The results are set forth in the Table.

EXAMPLE XV

A catalyst was made as in Example I however, strontium acetate was used instead potassium carbonate. The catalyst was impregnated by dissolving 45 grams of strontium acetate into 125 cc of distilled water and this was added in three steps to 65 grams of the catalyst of Example I. The impregnated catalyst was then dried at 140° C. for several hours and then treated as in Example VI. The catalyst was subjected to the hydrogen and carbon monoxide atmosphere as in Example I. The results were set forth in the Table.

Examples XIV and XV show that two alkaline earth metals, strontium and rubidium, are both active in promoting a cobalt-molybdenum catalyst to produce alcohols from a mixture of carbon monoxide and hydrogen.

EXAMPLES XVI THRU XIX (Comparative)

Catalysts were made as in Example I however, solutions of lithium acetate, sodium carbonate, magnesium acetate and calcium acetate were used, respectively, to impregnate the catalyst. The catalyst compositions are set forth in the Table, along with the results for alcohol production when these various catalysts were subjected to carbon monoxide and hydrogen as in Example VI at temperatures up to 360° C.

From the Table, it can be seen that these metals do not actively promote the production of lower alcohols from the carbon monoxide-hydrogen mixture, thus showing that only cesium, potassium, strontium and rubidium are useful alkali and alkaline earth metals for promoting the production of alcohols using a cobalt-molybdenum catalyst.

EXAMPLE XX

A catalyst was made by adding to 100 grams of alumina pellets, a solution containing 17.9 grams of cobalt nitrate, and 37.48 grams of chromium nitrate with drying at about 110° C. between additions. The amount of chromium was chosen so as to have approximately the same number of gram atoms of chromium in the final catalyst as gram-atoms of molybdenum in the catalysts of the previous examples. After all the solution was added, the alumina was dried at about 110° C. and then calcined for about 2 hours at 200° C., 1 hour at 375° and 3 hours at 475° C. The 109 grams of recovered catalyst was then treated with an aqueous solution of 16.4 grams of potassium carbonate and finally dried for 2 hours at about 110° C. The resulting catalyst was treated as in Example VI and subjected to the hydrogen and carbon monoxide atmosphere as in Example I, at temperatures up to 360° C. Results are set forth in the Table.

EXAMPLE XXI

A catalyst was made by adding to 100 grams of alumina an aqueous solution containing 26.7 grams of tungstic acid dissolved in 200 milliliters of water containing 35 milliliters of concentrated ammonium hydroxide. The amount of tungsten was chosen so as to have approximately the same number of gram-atoms of tungsten in the final catalyst as gram-atoms of molybdenum in the catalysts of the previous examples. The alumina was dried at about 110° C. After drying the impregnated alumina was calcined at 200° C. for 2 hours, 375° C. for 1 hour and then at 475° C. for 3 hours. A solution of containing 19.5 grams of cobalt nitrate was then added to the alumina in the same manner as the tungsten was added, and then dried and calcined as above. After calcination, the material was treated with an aqueous solution containing about 15% by weight of potassium carbonate and dried about 110° C. The catalyst was then treated as in Example VI and then subjected to the mixture of carbon monoxide and hydrogen as in Example I, at temperatures up to 360° C. The results are set forth in the Table.

From the Table it can be seen that the replacement of molybdenum by either chromium or tungsten significantly reduced the effectiveness of the catalyst for the production of alcohols. The lower alcohol production can be seen upon the substitution of either chromium or tungsten for molybdenum.

EXAMPLE XXII

A catalyst was made by dissolving 14.85 grams of molybdenum trioxide in 100 milliliters of water containing 45 milliliters of concentrated ammonium hydroxide. After cooling, a solution of 9.07 grams of cobalt nitrate was slowing added and the mixture was filtered. The filtrate was added in portions to 100 grams of a magnesia support with drying between additions of the solution. The impregnated magnesia support was then calcined for 2 hours at 200° C., 1 hours at 375° C. and then 3 hours at 475° C. After cooling the impregnated magnesia was treated with a 15% by weight aqueous solution of potassium carbonate and then dried at about 110° C. The impregnated catalyst was then treated as in Example VI and subjected to a hydrogen and carbon monoxide atmosphere as in Example I. The results are set forth in the Table.

EXAMPLE XXIII

An aqueous solution of 14.75 grams of cobalt nitrate, 17.75 grams of molybdenum trioxide and 40.0 grams of ammonium hydroxide was added to 100 grams of silica gel (grade 41) and then dried at about 110° C. The impregnated catalyst was then calcined for 2 hours at 200° C., then for 1 hour at 325° C. and then for 4 hours at 475° C. After calcination, the catalyst was impregnated with about a 15% by weight aqueous solution of potassium carbonate and then dried again at 110° C. The catalyst was then treated as in Example VI and then subjected to carbon monoxide and hydrogen as in Example I. The results are set forth in the Table.

Examples XXII–XXIII show that the cobalt-molybdenum catalyst promoted by potassium is effective for alcohol production when impregnated on a silica or magnesia substrate as well as on an alumina substrate.

EXAMPLE XXIV

A catalyst was prepared by impregnating 90 grams of a commercially available catalyst containing cobalt, molybdenum and nickel on an alumina carrier, sold by American Cyanamid, Stamford, Conn. under the name HDS-35. This catalyst has a surface area of about 230 square meters per gram. The catalyst was impregnated with a solution of 10 grams of potassium carbonate ($K_2CO_3$) dissolved in 50 cc of distilled water. This catalyst was then dried in an oven at a temperature of 125° C. for four hours. The composition of the catalyst is set forth in the Table. The catalyst was treated as in Example VI and then exposed to hydrogen flow of about 3.06 liters per minute and a carbon monoxide flow of about 1.53 liters per minute, at a pressure of about $6.9 \times 10^6$ Pa (1,000 psig). The results are set forth in the Table.

Example XXIV shows that nickel can be a component of the molybdenum-cobalt catalyst promoted by potassium and such a catalyst is active for the production of alcohols.

EXAMPLE XXV

A catalyst was prepared by dissolving 25.8 grams of ammonium molybdate in water and then adding this solution to 125 grams of alumina sold as Harshaw AL3945. After the addition of the solution, the alumina was dried at 115° C. and then calcined at about 345° C. for about 2 hours. The alumina was then impregnated with an aqueous solution of iron nitrate which was made by dissolving 22.7 grams of iron nitrate in water. The resulting catalyst was dried at 115° C., calcined for about 3 hours at 400° C. and then impregnated with a sufficient quantity of a solution of potassium carbonate so that the potassium carbonate comprised about 15% by weight of the catalyst. The resulting catalyst was then dried at about 115° C. The composition of the resulting catalyst is set forth in the Table.

10 cc of the above catalyst was diluted with 90 cc of alpha alumina and packed into a 2.5 centimeter ID tubular reactor, then subjected to the hydrogen and carbon monoxide mixture of Example I. The results of the reaction are set forth in the Table.

From the results of Example XXV it can be seen that a catalyst comprising molybdenum and iron on an alumina base with a preferred quantity of potassium is useful in producing the desired alcohols and also produces a useful ratio of alcohols containing 2 to 6 carbon atoms to methanol.

EXAMPLE XXVI

About 52.5 grams of potassium carbonate was dissolved into about 175 grams of distilled water. About 32 grams of this solution was added to about 42 grams of a catalyst made by American Cyanamid having a surface area of about 170 $m^2$/gram and designated HDS-9. The catalyst was then dried for several hours in a forced air oven in about 115° C.

About 10 cc of the above catalyst was diluted with about 90 cc of alpha alumina and packed into a 2.5 centimeter inside diameter tubular reactor. The catalyst was reduced for about 4 hours at about 400° C., at a pressure of about $1 \times 10^7$ Pa (1,500 psig), and at a hydrogen gas flow of about 2 liters per minute. The catalyst was then reacted as in Example I with the temperature, pressure, and GHSV set forth in the Table. The selectivity and alcohol production are set forth in the Table.

From the Table it can been seen that a catalyst comprising molybdenum and nickel on alumina and having the preferred quantity of potassium produces useful quantities of alcohol.

|  | EXAMPLE | | | | | | |
| --- | --- | --- | --- | --- | --- | --- | --- |
|  | I | II | III | IV | V | VIII | IX |
| Catalyst Composition |  |  |  |  |  |  |  |
| Wt % |  |  |  |  |  |  |  |
| $MoO_3$ | 10.7 | 10.5 | 9.6 | 9.7 | 7.6 | 7.7 | 0 |
| CoO | 3.7 | 3.6 | 3.4 | 3.1 | 2.8 | 0 | 2.5 |
| NiO |  |  |  |  |  |  |  |
| $Fe_2O_3$ |  |  |  |  |  |  |  |
| $Al_2O_3$ | 67.4 | 66.5 | 61.6 | 64.1 | 49.7 | 68.9 | 66.5 |
| Wt. % $K_2O$ | 2.26 | 3.58 | 5.93 | 9.18 | 11.21 | 8.95 | 8.95 |
| Wt. % $Cs_2O$ |  |  |  |  |  |  |  |
| Misc. wt. % |  |  |  |  |  |  |  |
| Wt. % Other Metal Oxides |  |  |  |  |  |  |  |
| $H_2$/CO Ratio | 2 | 2 | 2 | 2.0 | 2.0 | 2.0 | 2.0 |

-continued

| | | | | | | | |
|---|---|---|---|---|---|---|---|
| Temperature °C. | 343 | 343 | 343 | 343 | 343 | 343 | 343 |
| GHSV (HR$^{-1}$) | 28,000 | 28,000 | 28,000 | 28,000 | 28,000 | 20,000 | 28,000 |
| Pressure Pa | 1 × 10$^7$ | 1 × 10$^7$ | 1 × 10$^7$ | 1 × 10$^7$ | 1 × 10$^7$ | 1 × 10$^7$ | 1 × 10$^7$ |
| $\frac{\mu\text{-Mole K}}{M^2}$ | 1.74 | 2.76 | 4.58 | 7.09 | 8.65 | 11.9 | 8.3 |
| $\frac{\mu\text{-Mole Cs}}{M^2}$ | | | | | | | |
| $\frac{\mu\text{-Mole Alkali or Alkaline Earth}}{M^2}$ | | | | | | | |
| Selectivity (%) To: | | | | | | | |
| CO$_2$ | 40 | 41 | 41 | 44 | 46 | 48.7 | 46.3 |
| C$_1$–C$_6$ Hydrocarbons | 59 | 36 | 24 | 29 | 37 | 41.4 | 52.4 |
| MeOH | 0.8 | 13 | 13 | 9 | 4 | 4.3 | 0.5 |
| C$_2$–C$_6$ Alcohols | 0.1 | 9 | 21 | 19 | 13 | 5.6 | 0.8 |
| Alcohol Production (G/G-Hr) | 0.007 | 0.31 | 0.37 | 0.28 | 0.10 | 0.07 | 0.0004 |
| $\frac{\text{C}_2\text{–C}_6 \text{ Alcohols Wt. \%}}{\text{MeOH Liquids Wt. \%}}$ | 0.18 | 0.53 | 1.24 | 1.9 | 1.8 | 0.9 | 1.2 |
| C$_2$+Alc .Prod. (G/G-Hr) | 0.001 | 0.11 | 0.20 | 0.18 | 0.064 | 0.033 | 0.00022 |

| | EXAMPLE | | | | | | | |
|---|---|---|---|---|---|---|---|---|
| | X | XI | XII | XIII | XIV | XV | XVI | XVII |
| Catalyst Composition Wt % | | | | | | | | |
| MoO$_3$ | 9.6 | 9.2 | 8.2 | 7.5 | 7.8 | 7.4 | 11.1 | 8.6 |
| CoO | 3.3 | 3.2 | 2.9 | 2.6 | 2.5 | 2.4 | 3.2 | 3.1 |
| NiO | | | | | | | | |
| Fe$_2$O$_3$ | | | | | | | | |
| Al$_2$O$_3$ | 63.6 | 61.2 | 54.2 | 49.3 | 53.6 | 51 | 58.0 | 54.2 |
| Wt. % K$_2$O | | | | | | | | |
| Wt. % Cs$_2$O | 8.45 | 15.50 | 18.32 | 23.95 | | | | |
| Misc. wt. % Other Metal Oxides | | | | | 13.99 SrO | 18.71 Rb$_2$O | 2.25 Li$_2$O | 6.2 Na$_2$O |
| H$_2$/CO Ratio | 2.0 | 2.0 | 2.0 | 2.0 | 2.0 | 2.0 | 2.0 | 2.0 |
| Temperature °C. | 340 | 340 | 340 | 340 | 360 | 360 | 360 | 360 |
| GHSV (HR$^{-1}$) | 28,000 | 28,000 | 28,000 | 28,000 | 28,000 | 28,000 | 28,000 | 28,000 |
| Pressure Pa | 1 × 10$^7$ | 1 × 10$^7$ | 1 × 10$^7$ | 1 × 10$^7$ | 1 × 10$^7$ | 1 × 10$^7$ | 1 × 10$^7$ | 1 × 10$^7$ |
| $\frac{\mu\text{-Mole K}}{M^2}$ | | | | | | | | |
| $\frac{\mu\text{-Mole Cs}}{M^2}$ | | | | | 2.18 | 4.0 | 4.73 | 6.18 |
| $\frac{\mu\text{-Mole Alkali or Alkaline Earth}}{M^2}$ | 4.9 | 7.3 | 5.5 | 7.3 | | | | |
| Selectivity (%) To: | | | | | | | | |
| CO$_2$ | 41.7 | 41.9 | 44.8 | 47.1 | 49 | 50 | — | — |
| C$_1$–C$_6$ Hydrocarbons | 44.9 | 24.9 | 24.9 | 29.1 | 36 | 28 | — | — |
| MeOH | 7.8 | 11.2 | 10.5 | 6.8 | 8 | 6 | — | — |
| C$_2$–C$_6$ Alcohols | 5.1 | 18.7 | 19.0 | 16.4 | 6 | 15 | — | — |
| Alcohol Production (G/G Hr) | 0.15 | 0.56 | 0.39 | 0.20 | 0.11 | 0.27 | 0.04 | 0 |
| $\frac{\text{C}_2\text{–C}_6 \text{ Alcohols Wt. \%}}{\text{MeOH Liquids Wt. \%}}$ | 0.54 | 1.1 | 1.2 | 1.6 | 0.54 | 1.7 | 0.40 | — |
| C$_2$+Alc. Prod. (G/G Hr) | 0.052 | 0.29 | 0.21 | 0.12 | 0.038 | 0.17 | 0.011 | — |

| | EXAMPLE | | | | | | | |
|---|---|---|---|---|---|---|---|---|
| | XVIII | XIX | XX | XXI | XXII | XXIII | XXIV | XXV | XXVI |
| Catalyst Composition Wt % | | | | | | | | | |
| MoO$_3$ | 8.0 | 8.3 | 0 | 0 | 9.5 | 10.0 | 12.0 | 11.5 | 15.7 |
| CoO | 2.8 | 3.0 | 3.0 | 3.2 | 2.9 | 2.5 | 1.9 | | |
| NiO | | | | | 0 | 0 | 1.7 | 0 | 2.7 |
| Fe$_2$O$_3$ | | | | | | | | 2.6 | 0 |
| Al$_2$O$_3$ | 51.4 | 54.4 | 65.7 | 55.7 | 0 | 0 | 76 | 64.8 | 55.5 |
| Wt. % K$_2$O | | | | | 7.06 | 8.01 | 6.12 | 9.42 | 9.89 |

-continued

| Wt. % Cs₂O | | | | | | | | | |
|---|---|---|---|---|---|---|---|---|---|
| Misc. wt % | 4.83 MgO | 6.17 CaO | 8.48 K₂O | 8.95 K₂O | 64.7 MgO | 67.4 Si | | | |
| Wt. % Other Metal Oxides | 0 | 0 | 3.9 Cr₂O₃ | 17.5 WO₃ | | | | | |
| H₂/CO Ratio | 2.0 | 2.0 | 2.0 | 2.0 | 2 | 2 | 2 | 2 | 2 |
| Temperature °C. | 360 | 360 | 360 | 315 | 360 | 340 | 340 | 343 | 343 |
| GHSV(HR⁻¹) | 28,000 | 28,000 | 28,000 | 28,000 | 28,000 | 28,000 | 28,000 | 28,000 | 28,000 |
| Pressure Pa | 1 × 10⁷ | 1 × 10⁷ | 1 × 10⁷ | 1 × 10⁷ | 1 × 10⁷ | 1 × 10⁷ | 6.9 × 10⁶ | 1 × 10⁷ | 3.4 × 10⁶ |
| $\frac{\mu\text{-Mole K}}{M^2}$ | | | | | 74.9 | 2.8 | 5.6 | 8.5 | 12.3 |
| $\frac{\mu\text{-Mole Cs}}{M^2}$ | | | | | | | | | |
| $\frac{\mu\text{-Mole Alkali or Alkaline Earth}}{M^2}$ | 4.4 | 4.0 | 7.7 | 8.1 | | | | | |
| Selectivity (%) To: | | | | | | | | | |
| CO₂ | — | — | 58 | 49 | 55.3 | 50 | 22.8 | 36 | 36 |
| C₁–C₆ Hydrocarbons | — | — | 36 | 41 | 27.0 | 25 | 45.9 | 49 | 48 |
| MeOH | — | — | 3 | 5 | 4.5 | 6 | 12.1 | 4 | 8 |
| C₂–C₆ Alcohols | — | — | 4 | 5 | 12.7 | 18 | 15.4 | 11 | 6 |
| Alcohol Production (G/G-Hr) | 0 | 0 | 0.03 | 0.04 | 0.11 | 0.22 | 0.49 | 0.19 | 0.27 |
| $\frac{C_2\text{–}C_6 \text{ Alcohols Wt. \%}}{\text{MeOH Liquids Wt. \%}}$ | 0 | 0 | 0.9 | 0.8 | 1.9 | 2.0 | 0.99 | 2.1 | 0.5 |
| C₂+Alc. Prod. (G/G-Hr) | — | — | 0.014 | 0.018 | 0.072 | 0.15 | 0.24 | 0.13 | 0.09 |

The foregoing examples demonstrate that a process for the production of lower aliphatic alcohols from a mixture of carbon monoxide and hydrogen within the critical parameters for the prescribed catalyst modified or promoted with the specified alkali metal is effective for producing a high yield of $C_2$–$C_6$ aliphatic alcohols in relation to the production of methanol.

What is claimed is:

1. A method for preparing lower aliphatic alcohols characterized by producing a substantial proportion of aliphatic alcohols having from 2 to 6 carbon atoms which comprises reacting carbon monoxide and hydrogen in the presence of a catalyst at a temperature from about 240° to about 400° C., a pressure from about 500 to about 3000 psi and a gas hourly space velocity ranging from about 5,000 to 50,000, said catalyst consisting essentially of from about 5 to about 50 weight percent of molybdenum calculated as $MoO_3$ and from about 0.3 to about 15 weight percent of a metal selected from the group consisting of cobalt, iron and nickel, calculated as CoO, $Fe_2O_3$ and NiO respectively, and the balance a support, said catalyst having a surface area greater than about 125 m²/gm, and said catalyst being modified by the addition of an alkali metal promoter from the class consisting of potassium, cesium and rubidium in an amount ranging from about 2.2 to 10 micromoles of said alkali metal per square meter of catalyst surface area.

2. A method according to claim 1 in which said promoter is employed at a concentration ranging from about 2.5 to 9.0 micromoles.

3. A method according to claim 1 in which said catalyst is modified by the addition of 2.2 to 10.0 micromoles of cesium per square meter of catalyst surface area.

4. A method according to claim 1 in which said catalyst is modified by the addition of 2.2 to 10.0 micromoles of rubidium per square meter of catalyst surface area.

5. A method according to claim 1 in which said support is selected from the class consisting of alumina, silica, titania, magnesia, silica-alumina and boron phosphates.

6. A method according to claim 1 in which said support comprises from about 50 to 85 weight percent of said catalyst.

7. A method according to claim 1 in which said support is alumina and comprises from about 60 to 80 weight percent of said catalyst.

8. A method according to claim 1 in which the gas hourly space velocity ranges from about 10,000 to about 30,000.

9. A method according to claim 1 wherein the molar ratio of said hydrogen to carbon monoxide is in the range from about 50:1 to 0.1:1.

10. A method according to claim 1 in which the molar ratio of hydrogen to carbon monoxide ranges from about 20:1 to 0.5:1.

11. A method according to claim 1 in which said reaction temperature ranges from about 270° to 360° C.

12. A method according to claim 1 in which said catalyst has a surface area ranging from about 150 to 350 m²/gm.

13. A method according to claim 1 in which the weight ratio of the aliphatic alcohols having from 2 to 6 carbon atoms to methanol is at least 1.

14. A method according to claim 1 in which the weight ratio of the $C_2$–$C_6$ alcohols to methanol is in the range of 1.25–2:1.

15. A method according to claim 1 in which the metal components of a catalyst are in the free or combined form.

16. A method for preparing lower aliphatic alcohols in which the weight ratio of the $C_2$–$C_6$ alcohols to methanol is greater than 1 which comprises reacting carbon monoxide and hydrogen in the presence of a catalyst at a temperature from about 300° to 360° C., and a pressure from about 750 to 2500 psi and a gas hourly space velocity in the range from about 10,000 to 30,000, said catalyst consisting essentially of from about 7 to 30 weight percent of molybdenum calculated as $MoO_3$ and from about 0.5 to 10 weight percent of a metal or mixture of metals selected from the group consisting of cobalt, iron and nickel calculated as $CoO$, $Fe_2O_3$ and $NiO$ respectively, and the balance an alumina support, said catalyst having a surface area ranging from about 150 to 350 $m^2$/gm. and said catalyst being modified by the addition of an alkali metal promoter from the class consisting of potassium, cesium and rubidium in an amount ranging from about 2.5 to 9.0 micromoles of said alkali metal per square meter of catalyst surface area.

17. A method according to claim 16 in which said alumina support comprises from about 60 to 80 weight percent of said catalyst.

18. A method according to claim 16 in which said catalyst comprises from about 7 to 12 weight percent of molybdenum and from about 1.5 to 5 weight percent of a metal from the class consisting of cobalt, iron and nickel.

* * * * *